United States Patent
Aizman

(10) Patent No.: US 11,124,771 B2
(45) Date of Patent: Sep. 21, 2021

(54) MSC GROWTH PREDICTOR ASSAYS

(71) Applicant: SanBio, Inc., Mountain View, CA (US)

(72) Inventor: Irina Aizman, Mountain View, CA (US)

(73) Assignee: SanBio, Inc., Mountain View, CA (US)

( * ) Notice: Subject to any disclaimer, the term of this patent is extended or adjusted under 35 U.S.C. 154(b) by 200 days.

(21) Appl. No.: 16/222,836

(22) Filed: Dec. 17, 2018

(65) Prior Publication Data

US 2019/0127701 A1     May 2, 2019

Related U.S. Application Data

(63) Continuation of application No. PCT/US2017/042525, filed on Jul. 18, 2017.

(60) Provisional application No. 62/365,313, filed on Jul. 21, 2016.

(51) Int. Cl.
| | |
|---|---|
| *C12N 5/0775* | (2010.01) |
| *G01N 1/30* | (2006.01) |
| *G01N 33/569* | (2006.01) |

(52) U.S. Cl.
CPC ............. *C12N 5/0663* (2013.01); *G01N 1/30* (2013.01); *G01N 33/56966* (2013.01); *C12N 2501/42* (2013.01); *G01N 2001/305* (2013.01)

(58) Field of Classification Search
None
See application file for complete search history.

(56) References Cited

U.S. PATENT DOCUMENTS

| | | | |
|---|---|---|---|
| 5,486,359 | A | 1/1996 | Caplan et al. |
| 7,682,825 | B2 | 3/2010 | Dezawa et al. |
| 8,945,919 | B2 | 2/2015 | Mori et al. |
| 2003/0003090 | A1 | 1/2003 | Prockop et al. |
| 2010/0310529 | A1 | 12/2010 | Aizman |
| 2015/0272994 | A1 | 10/2015 | Kimbrel et al. |
| 2016/0115251 | A1 | 4/2016 | Nurcombe et al. |

FOREIGN PATENT DOCUMENTS

| | | |
|---|---|---|
| WO | WO 2009/087213 | 7/2009 |
| WO | WO 2018/017538 | 1/2015 |
| WO | WO 2016/161290 | 10/2016 |

OTHER PUBLICATIONS

Talele et al., "Expression of a-Smooth Muscle Actin Determines the Fate of Mesenchymal Stromal Cells", Stem Cell Reports, Jun. 2015, vol. 4, pp. 1016-1030. Supplementary Material, pp. 1-12 (Year: 2015).*
Deskins et al., "Human Mesenchymal Stromal Cells: Identifying Assays to Predict Potency for Therapeutic Selection", Stem cells Translational Medicine, 2013, vol. 2, pp. 151-158. (Year: 2013).*
Aizman el al., "Alpha-SMA Expression in Large Colonies of Colony-Forming Units-Fibroblast as an Early Predictor of Bone Marrow MSC Expandability," Cell Med, vol. 8, No. 3, pp. 79-85, Oct. 6, 2016.
Campagnoli et al., "Identification of Mesenchymal Stem/Progenitor Cells in Human Firsttrimester Fetal Blood, Liver, and Bone Marrow," Blood, 98(8):2396-2402 (2001).
Debnath et al., Proliferation and Differentiation Potential of Human Adipose* Derived Stem Cells Grown on Chitosan Hydrogel, PLoS ONE, vol. 10(3), e0120803, pp. 1-14, Mar. 6, 2015.
Dezawa et al. "Sciatic Nerve Regeneration in Rats Induced By Transplantation of In Vitro Differentiated Bone-Marrow Stromal Cells," The European Journal of Neuroscience 14(11):1771-1776 (2001).
Erices et al., "Mesenchymal Progenitor Cells in Human Umbilical Cord Blood," Br. J Haematol., 109(1):235-242 (2000).
Hou et al., "Induction of Umbilical Cord Blood Mesenchymal Stem Cells Into Neuron-Like Cells In Vitro," Int. J Hematol., 78(3):256-261 (2003).
Jiang et al., "Pluripotency of Mesenchymal Stem Cells Derived From Adult Marrow," Nature 418:41-49 (2002).
Pittenger et al., "Multilineage Potential of Adult Human Mesenchymal Stem Cells," Science 284(5411):143-147 (1999).
Prockop et al., "Marrow Stromal Cells as Stem Cells for Nonhematopoietic Tissues," Science 276(5309):71-74 (1997).
Talele et al., "Expression of alpha-Smooth Muscle Actin Determines the Fate of Mesenchymal Stromal Cells," Stem Cell Reports, vol. 4, No. 6, pp. 1016-1030, Jun. 9, 2015.
Cordeiro-Spinetti, Eric et al., "Human bone marrow mesenchymal progenitors: perspectives on an optimized in vitro manipulation", Frontiers in Cell and Developmental Biology, vol. 2, Mar. 27, 2014 (Mar. 27, 2014).

* cited by examiner

*Primary Examiner* — Laura Schuberg
(74) *Attorney, Agent, or Firm* — Levine Bagade Han LLP

(57) ABSTRACT

Methods for selecting lots of bone marrow stromal cells (MSCs) having a high proliferative capacity are provided. Such methods are useful in the manufacture of therapeutic derivatives of MSCs.

8 Claims, 11 Drawing Sheets ns is a continuation of International Patent
MSC GROWTH PREDICTOR ASSAYS

CROSS REFERENCE TO RELATED APPLICATIONS

This application is a continuation of International Patent Application No. PCT/US2017/042525 filed on Jul. 18, 2017, which claims the benefit of U.S. Provisional Application No. 62/365,313 filed on Jul. 21, 2016, the contents of which are hereby incorporated by reference in their entirety.

STATEMENT REGARDING FEDERAL SUPPORT

Not applicable.

FIELD

The present disclosure is in the field of stem cells, methods for propagation of stem cells, and methods for determining the proliferative ability of different batches of stem cells obtained from bone marrow.

BACKGROUND

Mesenchymal stromal cells (MSCs) were first detected in bone marrow (BM) cultures as cells that formed adherent clonal fibroblastic colonies and that were capable of undergoing more than 20 population doublings; hence they were named colony forming units-fibroblast (CFU-f). Friedenstein et al. (1970) *Cell Tissue Kinet* 3:393-403; Friedenstein et al. (1976) *Exp. Hematol.* 5:267-274. The ability of these culture-expanded cells to differentiate into bone, cartilage, reticular tissue and adipose tissue, and to transfer the hematopoietic microenvironment (Friedenstein et al. (1974) *Exp. Hematol.* 2:83-92; Owen & Friedenstein (1988) *Ciba Found. Symp.* 136:42-60), along with their potent secretome (e.g., Paul & Anisimov (2013) *Biochimie* 95:2246-2256) and immunomodulatory properties (e.g. Menard & Tarte (2013) *Stem Cell Res. Ther.* 4:64-69) have brought them to the frontier of cell therapeutic efforts. More than 350 clinical trials currently use expanded mesenchymal stromal cells from bone marrow, or other sources, as potential treatments for various skeletal, degenerative, and immune disorders.

Large cell lots of allogeneic MSCs can be manufactured for "off-the shelf" use on a number of patients. The manufacturing of large BM MSC lots, however, can sometimes be challenging because of the high variability in the growth potential of MSCs derived from different BM donors. Zhukareva et al. (2010) *Cytokine* 50:317-321; Wegmeyer et al. (2013) *Stem Cells Dev.* 22:2606-2618; DiGirolamo et al. (1999) *Br. J. Haematol.* 107:275-281. It would be therefore advantageous to have methods for predicting MSC culturing outcome; thereby allowing the manufacturer to terminate unsuccessful lots early in the manufacturing process.

A basic assay for characterizing BM MSCs is the CFUf assay, which determines the number of clonogenic adherent cells (CFUf) within the BM preparation. At low BM cell plating densities, that ensure linearity between numbers of plated cells and resulting colonies, the colony forming efficiency (CFE; e.g., the number of colonies per $10^5$ plated cells) is dependent on the donor, the method for harvesting the BM specimen, cell isolation steps (e.g., washing), and the culturing protocol. Kuznetsov et al. (1997) *Br. J. Haematol.* 97:561-570; Latsinik et al. (1990) *Biull. Eksp. Biol. Med.* 110:519-522; Mannello & Tonti (2007) *Stem Cells* 25:1603-1609. Seven to ten days after plating, cultures contain colonies that vary greatly in size. CFUfs represent a mixture of stem cells, intermediate progenitors and committed progenitors; the cells are typically distinguished based on the potency of their colonies to undergo single, bi- or tri-lineage mesenchymal differentiation. It is generally believed that, in culture, stem cells are more prolific than both intermediate and committed progenitors, but have a longer lag period (before they begin dividing) after BM explantation than committed progenitors. Cordeiro-Spinetti et al. (2014) *Front. Cell Dev. Biol.* 2:7-15. In light of these differences between the time after plating at which division begins, and the rate of division (which together determine eventual proliferative capacity); between stem cells and more differentiated cells; a number of assays have been proposed as predictors of MSC growth potential. These include the tri-lineage differentiation potential (i.e., to chondrocytes, adipocytes and osteocytes) of colonies (Russell et al. (2011) *Biotechnol. Bioeng.* 108:2716-2726; Bertolo et al. (2016) *J. Tissue Eng. Regen. Med.* 10:149-161); colony forming efficiency after the first passage (DiGirolamo et al. (1999) supra), extent of proliferation and viability at early passages (Deskins et al. (2013) *Stem Cells Transl. Med.* 2:151-158); and cell motility as a marker of multipotent (stem) cells (Bertolo et al. (2015) *Stem Cells Transl. Med.* 4:84-90). However, these approaches require culturing of MSCs for multiple passages and are laborious, which makes them impractical as a rapid and simple growth predictor for cell manufacturing.

SUMMARY

Disclosed herein are rapid and reliable methods for predicting the growth potential (i.e. the proliferative capacity) of mesenchymal stromal cells early in their production process (i.e., in the colony-formation stage). The methods utilize assays of differentiation and cell number, in the same cell colony, in lightly fixed and permeabilized cells. In certain embodiments, levels of alpha-smooth muscle actin (α-SMA) provide a readout for the degree of differentiation, with lower α-SMA levels correlated with a less differentiated cell type. In certain embodiments, lactate dehydrogenase (LDH) activity provides a readout for cell number, with higher LDH activity correlated with higher cell number.

Because MSCs are used in the manufacture of a number of therapeutic cell types, and because MSC growth is variable from lot-to-lot, the methods provided herein allow the convenient selection of MSC lots most suitable for the manufacture of therapeutic derivatives of MSCs for use in cell therapy. An added advantage is that selection can be made shortly after initial culture of the cells; thereby reducing the time needed to determine whether a lot is suitable for manufacturing purposes.

Accordingly, provided herein are methods for selecting a lot of mesenchymal stromal cells (MSCs) with a high proliferative capacity (or a high growth potential), from among a plurality of lots of bone marrow suspension; the methods comprising (a) separately plating a sample of cells from each lot of bone marrow suspension at low density; (b) culturing the separately plated cells to form single colonies; (c) measuring, for each lot of cultured MSCs (i) the degree of differentiation of the cells in the colonies and (ii) the percentage of large colonies in each culture; and (d) selecting a lot or lots whose cultures exhibit (i) a lower degree of differentiation compared to other lots, and (ii) a higher percentage of large colonies compared to other lots; wherein said lot or lots whose cultures have a lower degree of differentiation and higher percentage of large colonies, compared to other lots being tested, have high proliferative capacity or high growth potential.

To test a lot of bone marrow cells, cells from the bone marrow lot are cultured (e.g., in a microtiter plate) at a density low enough that not every well in the plate contains a colony; making it likely that any well that does contain a colony contains only a single colony. The contents of the wells are then assayed for both degree of cell differentiation and colony size. Wells that do not contain colonies are sorted for background determination. Using a predetermined threshold for colony size (described elsewhere herein), the number of large colonies in the culture is determined. The values for average degree of differentiation of cells in the culture, and percentage of large colonies in the culture are then used to select the lots with the highest proliferative capacity or growth potential.

In certain embodiments, the degree of differentiation that is measured is the degree of myofibroblast differentiation.

In additional embodiments, the degree of differentiation is determined by measuring levels of alpha-smooth muscle actin (αSMA), transforming growth factor beta (TGF-β) and/or the ED-A domain of fibronectin; wherein lower αSMA, TGF-β and/or ED-A domain levels are positively correlated with a lower degree of differentiation.

In one embodiment, the degree of differentiation is determined by measuring levels of alpha-smooth muscle actin (αSMA). αSMA levels can be determined by contacting a colony with an anti-αSMA antibody and measuring immunoreactivity of the colony with the antibody; and αSMA levels can be expressed, for example as the concentration (e.g., in ng/ml) of reactive anti-αSMA antibody. In certain embodiments, the level of αSMA in a colony is normalized to the number of cells in the colony.

In certain embodiments, the number of cells in a colony is represented by the level of LDH activity in the colony. Colonies having levels of LDH activity greater than 0.4 mU/ml are considered large colonies, for the purposes of this disclosure.

In certain embodiments, the percentage of large colonies in a culture is determined by measuring the amount of lactate dehydrogenase (LDH) in colonies present in the culture, wherein a colony with a LDH level of greater than 0.4 mUnits/ml is considered a large colony. In additional embodiments, the percentage of large colonies in a culture is determined by counting the number of cells in colonies present in the culture, wherein a colony with 1,000 cells or more is considered a large colony.

In certain embodiments, only large colonies are selected for analysis. In these embodiments, large colonies (i.e., colonies having LDH activity levels of >0.4 mU/ml) are identified, and αSMA levels in the large colonies are determined. The average αSMA levels (expressed, e.g., as ng/ml of reactive antibody) in the large colonies are normalized to the average LDH activity levels in the large colonies (expressed as mU LDH activity per ml) and this value (Av (αSMA/LDH)$_{LC}$) is expressed as a function of the percentage of large colonies in the culture. Cultures with a combination of low Av(αSMA/LDH)$_{LC}$ values (e.g., <100 ng/ml reactive antibody) and high percentage of large colonies (e.g., >40%) are identified as being derived from a cell sample with a high proliferative capacity.

In certain embodiments, measurements of the degree of differentiation of colonies, and of the percentages of large colonies, are conducted ten days after plating the cells.

As noted previously, MSCs are used in the manufacture of a number of different therapeutic cell types. Accordingly, in certain embodiments, a lot of bone marrow cells (e.g., MSCs) that have been selected for high proliferative capacity or high growth potential are used in a process for manufacturing a therapeutic derivative of MSCs. Certain manufacturing processes require large amounts of cells. Accordingly, in certain embodiments, cells from a selected lot or lots of bone marrow, containing MSCs with high proliferative capacity, are grown in mass culture.

In additional embodiments, cells from selected lots, that are growing in mass culture, are transfected with an exogenous nucleic acid. In certain embodiments, the exogenous nucleic acid is a polynucleotide comprising sequences encoding a Notch intracellular domain, wherein the polynucleotide does not encode full-length Notch protein.

Also provided herein is a method for identifying a lot of mesenchymal stromal cells (MSCs) having a high proliferative capacity, wherein the method comprises (a) plating a sample of MSCs at low density; (b) culturing the MSCs so that single colonies are formed; (c) measuring αSMA levels in each colony; (d) measuring LDH activity in each colony; (e) determining the number of large colonies in the culture; (f) normalizing the level of αSMA to the level of LDH activity in the large colonies, to obtain an average αSMA/LDH value for the large colonies; and (g) expressing the average αSMA/LDH value for the large colonies as a function of the percentage of large colonies in the culture; wherein a lot of MSCs that provides a culture characterized by a low average αSMA/LDH value (e.g., <100 ng/ml reactive antibody), and a high percentage of large colonies (e.g., >40%), is a lot having a high proliferative capacity.

Also provided herein are methods for simultaneous assay, in a population of cells, of cell number and levels of a cellular marker, the methods comprising (a) fixing the cells; (b) permeabilizing the fixed cells; (c) detecting levels of LDH activity in the fixed cells; and (d) detecting levels of the marker in the fixed cells.

In certain embodiments, the cells are fixed with paraformaldehyde. In additional embodiments, fixation with paraformaldehyde is conducted for 20 minutes.

In certain embodiments, the cells are permeabilized with Triton-X100. In additional embodiments, permeabilization is conducted for 20 minutes.

In certain of the assays disclosed herein, LDH levels are used as a surrogate marker for cell number. In some embodiments, LDH activity is measured by formation of NADH resulting from conversion of lactate to pyruvate. In certain embodiments, formation of NADH is coupled to conversion of a tetrazolium compound into a formazan compound. The tetrazolium compound can be, for example, 2-(4-iodophenyl)-3-(4-nitrophenyl)-5-phenyl-2H-tetrazolium (INT).

The cellular marker can be any molecule, including but not limited to nucleic acid (DNA or RNA), protein, phospholipid, glycoprotein, etc. In certain embodiments, the marker is a protein; in additional embodiments, the protein is alpha-smooth muscle actin (αSMA). Detection of a marker can be by any method known in the art, e.g., hybridization for nucleic acids; immunological detection for proteins, phospholipids, glycoproteins, etc. In certain embodiments, the marker is a polypeptide or protein (e.g., αSMA) and levels of the marker are detected immunologically. In some embodiments of the assays described herein, an antibody is used for immunological detection. In additional embodiments, the antibody is conjugated to a detection moiety. In certain embodiments, the detection moiety is horseradish peroxidase (HRP). In embodiments in which a HRP-conjugated antibody is -tetramethylbenzidine (TMB).

DETAILED DESCRIPTION

Figure 1A:
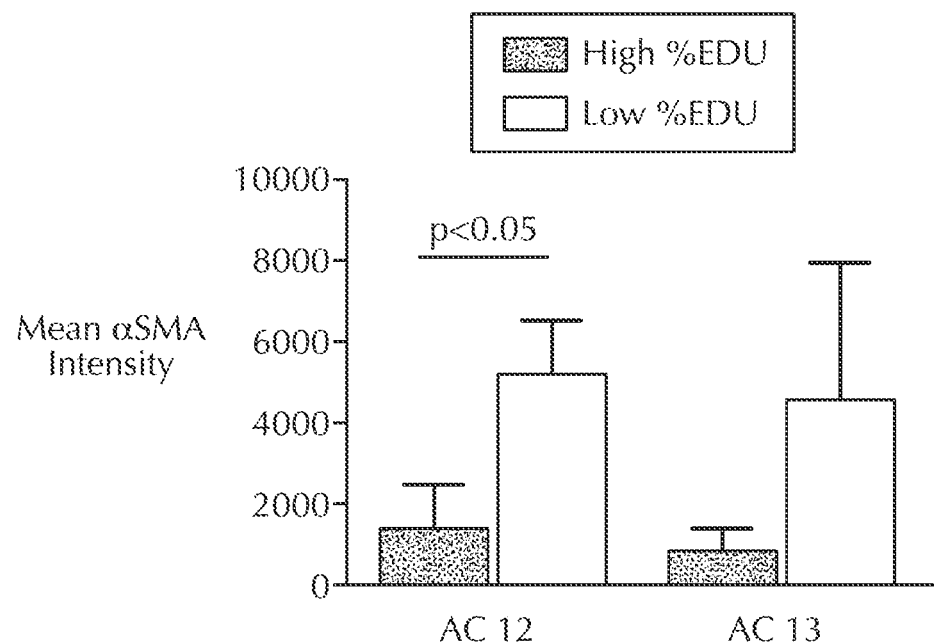
FIG. 1A shows levels of α-SMA immunoreactivity (presented as mean fluorescence intensity) in MSC colonies containing the highest (stippled bars) and lowest (white bars) percentage of EDU-positive cells in two lots (AC12 and AC13) of cultured bone marrow cells. Error bars indicate standard deviation among 3-4 colonies per group.

Practice of the present disclosure employs, unless otherwise indicated, standard methods and conventional techniques in the fields of cell biology, toxicology, molecular biology, biochemistry, cell culture, immunology, oncology, recombinant DNA and related fields as are within the skill of the art. Such techniques are described in the literature and thereby available to those of skill in the art. See, for example, Alberts, B. et al., "Molecular Biology of the Cell," 5th edition, Garland Science, New York, N.Y., 2008; Voet, D. et al. "Fundamentals of Biochemistry: Life at the Molecular Level," 3' edition, John Wiley & Sons, Hoboken, N.J., 2008; Sambrook, J. et al., "Molecular Cloning: A Laboratory Manual," 3rd edition, Cold Spring Harbor Laboratory Press, 2001; Ausubel, F. et al., "Current Protocols in Molecular Biology," John Wiley & Sons, New York, 1987 and periodic updates; Freshney, R. I., "Culture of Animal Cells: A Manual of Basic Technique," 4th edition, John Wiley & Sons, Somerset, N J, 2000; and the series "Methods in Enzymology," Academic Press, San Diego, Calif.

For the purposes of the present disclosure, the terms: "growth potential" and "proliferative capacity" are used interchangeably to refer to the predicted rate of cell growth in cultures that originate from a particular lot of cells (e.g., MSCs). In lots with a high growth potential or a high proliferative capacity, the cells grow rapidly, with short doubling times. In lots with a low growth potential or a low proliferative capacity, the cells grow more slowly, with longer doubling times.

Thus, cells with a high proliferative capacity can have a doubling time of, for example, 4 days, 3.5 days, 3 days, 2.5 days, 48 hours, 36 hours, 24 hours, 18 hours, 12 hours, 6 hours, or any value therebetween.

The terms "normalized αSMA" refers to the amount of αSMA in a cell colony divided by the LDH level of the colony (surrogate for cell number), where the amount of αSMA is expressed as ng/ml of anti-αSMA antibody that binds to the colony in an immunoassay, and LDH levels are expressed as mUnits/ml as defined in the LDH Cytotoxicity Detection assay (Clontech Laboratories, Mountain View, Calif.). The normalized αSMA value is a surrogate for average αSMA level per cell for a given colony.

The term "Av(αSMA/LDH)$_{LC}$" refers to the average of the normalized αSMA values (i.e., average αSMA/LDH) obtained for large colonies (LDH>0.4 mU/ml) in a culture of MSCs.

For the purposes of the present disclosure, a "large colony" is a cell colony in which, when all of the cells in the colony are assayed for intracellular LDH activity, the total intracellular LDH activity value of the cells in the colony is greater than 0.4 milliUnits per milliliter, as defined by the LDH Cytotoxicity Detection kit (Clontech Laboratories, Mountain View, Calif.).

The percentage of large colonies in a culture is the percentage of colonies having LDH activity values greater than 0.4 milliUnits/ml.

"Mesenchymal stromal cells" ("MSCs") refer to adherent, non-hematopoietic pluripotent cells obtained from bone marrow. These cells are variously known as mesenchymal stem cells, mesenchymal stromal cells, marrow adherent stromal cells, marrow adherent stem cells and bone marrow stromal cells. MSCs can also be obtained from, e.g., umbilical cord blood, adipose tissue, dental pulp, Wharton's jelly, and various types of connective tissue.

Exemplary disclosures of MSCs are provided in U.S. Patent Application Publication No. 2003/0003090; Prockop (1997) *Science* 276:71-74 and Jiang (2002) *Nature* 418:41-49. Methods for the isolation and purification of MSCs can be found, for example, in U.S. Pat. No. 5,486,359; Pittenger et al. (1999) *Science* 284:143-147 and Dezawa et al. (2001) *Eur. J. Neurosci.* 14:1771-1776. Human MSCs are commercially available (e.g., BioWhittaker, Walkersville, Md.) or can be obtained from donors by, e.g., bone marrow aspiration, followed by selection for adherent bone marrow cells. See, e.g., WO 2005/100552.

MSCs can also be isolated from umbilical cord blood. See, for example, Campagnoli et al. (2001) *Blood* 98:2396-2402; Erices et al. (2000) *Br. J. Haematol.* 109:235-242 and Hou et al. (2003) *Int. J. Hematol.* 78:256-261. Additional sources of MSCs include, for example, menstrual blood and placenta.

Cell Culture and Transfection

Standard methods for cell culture are known in the art. See, for example, R. I. Freshney "Culture of Animal Cells: A Manual of Basic Technique," Fifth Edition, Wiley, New York, 2005.

Methods for introduction of exogenous DNA into cells (i.e., transfection), and methods for selection of cells comprising exogenous DNA, are also well-known in the art. See, for example, Sambrook et al. "Molecular Cloning: A Laboratory Manual," Third Edition, Cold Spring Harbor Laboratory Press, 2001; Ausubel et al., "Current Protocols in Molecular Biology," John Wiley & Sons, New York, 1987 and periodic updates.

In certain embodiments of the instant disclosure, lots of cells with high proliferative capacity, identified by the methods disclosed herein, are cultured in mass culture; for example, in the manufacture of a therapeutic derivative of MSCs. In certain embodiments, cells in mass culture, selected for high growth potential as disclosed herein, are transfected with exogenous DNA. In certain embodiments, cells with a high proliferative capacity, growing in culture, are transfected with sequences encoding a Notch intracellular domain (that do not encode full-length Notch protein) as disclosed, for example, in U.S. Pat. No. 7,682,825 (for the preparation of cells denoted "neural precursor cells" therein); U.S. Pat. No. 8,945,919 (for the preparation of cells denoted "neural regenerating cells" therein); U.S. Patent Application Publication No. 2010/0310529 (for the preparation of cells denoted "differentiation-restricted cells" therein); and WO 2016/161290 (for the preparation of cells denoted "descendants of NICD transiently-transfected MSCs" or "DNTT-MSCs" therein).

Differentiation Markers

The inventors have found that MSC cultures with a lower degree of differentiation have a higher proliferative capacity; and therefore the degree of differentiation of the cells in a culture of MSCs can be used to predict the proliferative capacity of the cell lot from which the culture is derived. Accordingly, as part of the methods disclosed herein, the degree of differentiation of cells in a culture of MSCs is determined. Any marker of MSC differentiation, as known in the art, can be used. In certain embodiments, a marker of myofibroblast differentiation can be used. For example, alpha-smooth muscle actin (αSMA), transforming growth factor beta (TGF-β) and/or the ED-A domain of fibronectin can be used as differentiation markers; wherein lower αSMA, TGF-β and/or ED-A domain levels are positively correlated with a lower degree of differentiation.

In certain embodiments, alpha smooth muscle actin (αSMA) is used as an MSC differentiation marker. αSMA is a contractile actin isoform, a hallmark of vascular smooth muscle cells and myofibroblasts which differentiate from many mesenchymal cell types in response to tissue injury and repair. Hinz (2007) *J. Investig. Dermatol.* 127:526-537. In the wound, myofibroblasts produce extracellular matrix, and reorganize, contract, and harden the matrix, which in turn induces further αSMA expression. Thus αSMA expression is stimulated by increased stiffness of the substrate on which the myofibroblast is growing. In cultured MSCs, αSMA co-localizes with stress fibers that typically develop in these cells during culturing. Charbord et al. (1990) *Exp. Hematol.* 18:276-282.

Sorting passaged MSCs by cell size (small and large cell populations) concomitantly sorts them by expression of αSMA (low and high, correspondingly), and by clonal and differentiation potential (high and low, correspondingly). Moreover, knockdown of αSMA expression, or plating cells onto a soft surface, restores clonogenicity and differentiation potential. Talele et al. (2015) *Stem Cell Reports* 4:1016-1030. Thus, to a certain degree, αSMA expression in early MSC cultures can be regarded as a consequence of culturing these mechanosensitive cells on a stiff plastic surface. Hinz (2010) *J. Biomech.* 43:146-55.

Any method known in the art can be used to measure the levels of αSMA (or of any other MSC differentiation marker) in colonies of MSCs in culture. For example, levels of αSMA mRNA can be determined by hybridization or PCR-based methods. Levels of αSMA polypeptide can be determined immunologically Immunological protein detection methods are well-known in the art. In certain embodiments, levels of αSMA protein are detected in situ in isolated colonies using an anti-αSMA antibody conjugated to a detection moiety. The detection moiety can be radioactive, colorimetric, fluorescent, etc., as known in the art. Alternatively, a ligand such as, for example, biotin, can be used as a detection moiety.

In certain embodiments, αSMA levels are detected in situ in MSC colonies using an anti-αSMA antibody. In certain embodiments, αSMA levels are detected in situ in MSC colonies using an anti-αSMA antibody conjugated to a detection moiety. Detection moieties for use in immunohistochemical procedures are known in the art. In certain embodiments, αSMA levels are detected in situ in MSC colonies using an anti-αSMA antibody conjugated to horseradish peroxidase (HRP). Various HRP substrates, that are converted to colored products by HRP are known in the art. In certain embodiments, αSMA immunoreactivity is detected using 3,3',5,5'-tetramethylbenzidine (TMB), which is converted by HRP to a blue product.

Levels of αSMA, or of any other detection marker, can be expressed in any convenient units such as, for example, concentration of antibody that reacts with the cells in the colony. In certain embodiments, αSMA levels are expressed as ng/ml of reactive antibody.

It is clear that any other differentiation marker can be detected and quantitated using, for example, an antibody specific to the differentiation marker, optionally conjugated to any detection moiety known in the art.

Determination of Cell Number and Percentage of Large Colonies

In the methods disclosed herein, the number of large colonies in a culture of MSCs is one of the factors used to determine the growth potential (i.e., proliferative capacity) of the cell lot from which the culture was obtained. Accordingly, the present disclosure provides methods for determining cell number and using said determination in a process for predicting growth potential of a cell lot.

Any method known in the art for determining cell number can be used in the methods described herein. Exemplary methods include counting the number of cells in a colony and counting the number of nuclei in a colony or in a culture, e.g., by phase-contrast microscopy or by the use of nucleus-specific dyes (e.g., Hoechst 33342).

In certain embodiments, intracellular lactate dehydrogenase (LDH) activity is used as an indicator of cell number. Methods for determining intracellular LDH are known in the art, for example the LDH Cytotoxicity Detection kit (Clontech Laboratories, Mountain View, Calif.) can be used. The inventors have determined that a colony having a value of 0.4 mU/ml intracellular LDH activity contains approximately 1,000 cells, and have selected these values (0.4 mU/ml intracellular LDH activity or $1 \times 10^3$ cells) as thresholds for characterizing a cell colony as a "large colony," for use in the methods described herein. In particular, the percentage of large colonies in a culture is determined, and normalized αSMA levels in the large colonies are calculated, as part of the method for predicting growth potential of a lot of MSCs.

Normalization of αSMA Levels

To enhance the predictive value of the methods described herein, the αSMA level in a colony was normalized to the value of intracellular LDH activity in that colony, to provide a surrogate value for αSMA level per cell. In one embodiment for obtaining this normalized αSMA per cell value, αSMA levels are expressed as ng/ml of anti-αSMA antibody bound to a colony; and LDH levels are expressed as mU/ml LDH activity (where Units are defined according to the LDH Cytotoxicity Detection kit (Clontech Laboratories, Mountain View, Calif.).

In certain embodiments, this normalized αSMA/LDH value is obtained only for the large colonies (defined as described herein) in a culture, to provide a Av(αSMA/LDH)$_{LC}$ value. This Av(αSMA/LDH)$_{LC}$ value is then expressed as a function of the percentage of large colonies in the culture. A culture having a high percentage of large colonies, and a low Av(αSMA/LDH)$_{LC}$ value, is indicative that the cell lot from which the culture was derived has a high proliferative capacity or growth potential. For example, cell lots having a high proliferative capacity will generate cultures having 50% or more large colonies. In certain embodiments cell lots having a high proliferative capacity will generate cultures having 55% or more, 60% or more, 65% or more, 70% or more, 75% or more, 80% or more, 85% or more, 90% or more, 95% or more, or 98% or more large colonies.

In certain embodiments, the Av(αSMA/LDH)$_{LC}$ value is an arbitrary quantity obtained by dividing ng/ml reactive anti-αSMA antibody in a large colony by mU/ml intracellular LDH activity in the same large colony; and obtaining the average of that quotient for all large colonies in the culture. In these embodiments, cell lots having a high proliferative capacity (or a high growth potential) have a Av(αSMA/LDH)$_{LC}$ value of 125 or less. In additional embodiments, cell lots having a high proliferative capacity (or a high growth potential) have a Av(αSMA/LDH)$_{LC}$ value of 120 or less, 110 or less, 100 or less, 90 or less, 80 or less, 70 or less, 60 or less or 50 or less.

In certain embodiments, only one of the two parameters (Av(αSMA/LDH)$_{LC}$ value or percentage large colonies) is used to predict proliferative capacity of a cell lot. However, optimum predictive value is obtained when both parameters are used.

Assay of Cell Number and Differentiation Marker in the Same Colony ("ALC" Assay)

To identify cell lots with a high proliferative capacity (or high growth potential); the present disclosure provides methods for assaying both cell number and levels of a marker in a cell culture. In particular, cultures are plated at low density (e.g., in a culture dish or in wells of a microtiter plate) so that dispersed single colonies grow up from the plated cells. For any individual colony, the assays disclosed herein are able to measure both the number of cells in the colony and the level of a marker molecule in the colony.

A marker molecule can be any molecule that is present in a cell or characteristic of a particular cell type; and can be, for example, a nucleic acid (DNA or RNA) or a polypeptide (i.e., a protein). In certain embodiments, the marker is indicative of the degree of differentiation of a cell (i.e., a differentiation marker). The marker can be detected by any method known in the art, e.g., hybridization or PCR-based methods for detection of nucleic acids, and immunological methods for detection of proteins. In certain embodiments of the methods disclosed herein, alpha smooth muscle actin (αSMA) is used as a marker for the degree of differentiation of MSCs, with higher αSMA levels being indicative of more highly differentiated cells.

Methods for determining cell number are known in the art and include, for example, simple cell counting, counting of nuclei, flow cytometry, measurement of DNA concentration and measurement of metabolic activity. In certain embodiments, levels of lactate dehydrogenase (LDH) activity in a colony are used as a surrogate for the number of cells in a colony. Methods for measurement of LDH activity are known in the art. In certain embodiments, LDH activity is measured by formation of NADH resulting from conversion of lactate to pyruvate; and the formation of NADH is coupled to the conversion of a first, colorless compound into a compound that can be detected photometrically or fluorimetrically. In certain embodiments, the first compound is a tetrazolium compound. In certain embodiments, the tetrazolium compound is 2-(4-iodophenyl)-3-(4-nitrophenyl)-5-phenyl-2H-tetrazolium (INT).

Provided herein are methods for determination, in the same colony of cells, of both cell number and levels of a marker molecule. The methods comprise culturing cells at low density so that dispersed single colonies are generated, fixing the cultured cells, permeabilizing the fixed cells, measuring cell number (or measuring a surrogate for cell number, such as the intracellular LDH activity of the cells in a colony) and detecting levels of the marker molecule.

To allow determination of both cell number and levels of a marker molecule in the same colony, parameters for fixation and permeabilization are provided herein. In certain embodiments, cells are fixed with paraformaldehyde. The concentration of paraformaldehyde used for fixation can be, for example, 0.5%, 1%, 1.5%, 2%, 2.5%, 3%, 3.5%, 4%, 4.5%, 5%, 5.5%, 6% or any value therebetween; depending on the cell type and culture conditions. In certain embodiments, cells are permeabilized with Triton-X100. The concentration of Triton-X100 used for permeabilization can be, for example, 0.05%, 0.1%, 0.15%, 0.2%, 0.25%, 0.3%, 0.35%, 0.4%, 0.45%, 0.5% or any value therebetween; depending on the cell type and culture conditions.

In certain embodiments, cells are fixed with 4% paraformaldehyde for 20 min at room temperature, and subsequently permeabilized with 0.2% Triton-X100 for 20 min at room temperature. Concentrations of the fixative and/or permeabilizing agent, as well as the fixation and permeabilization times, can be varied as necessary, depending on the cell type and other relevant considerations. For example, cells can be fixed for 5, 10, 15, 20, 25, 30, 40, 45, 50 or 60 minutes and can be permeabilized for 5, 10, 15, 20, 25, 30, 40, 45, 50 or 60 minutes. Fixatives other than paraformaldehyde (as are known in the art) and permeabilizing agents other than Triton (as are known in the art) can be used in the methods disclosed herein. It is within the skill of the art to define appropriate fixation and permeabilization times for other fixatives and permeabilizing agents.

Measurement of cell number and levels of a differentiation marker in a colony of cells can be conducted at any time after plating of the cells that gave rise to the colony. For example, the measurements can be conducted one day, 2 days, 3 days, 4 days, 5 days, 6 days, 7 days, 8 days, 5 days, 10 days, 11 days, 12 days, 13 days, 14 days, 15 days, 20 days, 25 days, 30 days, or any interval therebetween. In certain embodiments, the measurement of cell number and levels of a differentiation marker in a colony of cells is conducted ten days after the cells have been plated.

Manufacturing Processes

One of the objectives of the methods disclosed herein is to allow the selection of lots of bone marrow cells with high growth potential and/or high proliferative capacity, for the manufacture of therapeutic derivatives of MSCs, early in the process of culturing the bone marrow cells. One such therapeutic derivative is manufactured by transfecting cultured MSCs with a nucleic acid that encodes a Notch intracellular domain (NICD). See, for example, U.S. Pat. No. 7,682,825 (for the preparation of cells denoted "neural precursor cells" therein); U.S. Pat. No. 8,945,919 (for the preparation of cells denoted "neural regenerating cells" therein); U.S. Patent Application Publication No. 2010/0310529 (for the preparation of cells denoted "differentiation-restricted cells" therein); and WO 2016/161290 (for the preparation of cells denoted "descendants of NICD transiently-transfected MSCs" or "DNTT-MSCs" therein); the disclosures of which are incorporated by reference herein for the purpose of describing processes for manufacturing NICD-transfected MSCs for use in cell therapy.

Accordingly, in certain embodiments, cells from a selected lot or lots of bone marrow, containing MSCs with high proliferative capacity, are grown in mass cultures and transfected with an exogenous nucleic acid. In certain embodiments, the exogenous nucleic acid is a polynucleotide comprising sequences encoding a Notch intracellular domain, wherein the polynucleotide does not encode full-length Notch protein.

EXAMPLES

Example 1: Preparation and Culture of Bone Marrow Stromal Cells

Bone marrow aspirates from healthy human donors were purchased from Lonza (Allendale, N.J.) or AllCells (Alameda, Calif.) and delivered overnight in cold packs. The aspirate sample (1-3 ml) was diluted 3 times in MSC growth medium (alpha minimal essential medium (aMEM, Mediatech, Tewksbury, Mass.) supplemented with 10% fetal bovine serum (HyClone, Logan, Utah, lot selected for MSC growth), GlutaMAX (Invitrogen, Carlsbad, Calif.), and penicillin/streptomycin and centrifuged at 1200 rpm for 8 min. The supernatant was carefully removed and the pellet was resuspended in a volume equal to the volume prior to centrifugation. Aliquots were removed and diluted in Erythrocyte Lysis Reagent (Sigma, St. Louis, Mo.) for white blood cell (WBC) counts. These washed bone marrow cells were cultured for use in microtiter assays (Examples 4 and 5) and for generating mass cultures (Example 6).

For analysis of CFUf colonies, washed bone marrow cells (obtained as described in the preceding paragraph) were resuspended at a concentration of $6.6 \times 10^4$ WBCs/ml and plated (100 µl of cell suspension per well) into 96-well black microplates with clear bottoms (Costar®); two rows were left empty for standards and controls. Plating at this cell concentration resulted in growth of colonies in less than 30% of wells; thus ensuring a low probability of having more than 1 colony per well. On the 10th day after plating, the ALC assay was conducted on cells that had been grown in the 96-well microplates.

To generate mass cultures, bone marrow cells, obtained and processed as described supra, were resuspended and plated at approximately $2$-$4 \times 10^5$ WBCs/cm$^2$ into a T75 flask. On the third day after plating, the medium was changed, resulting in removal of the majority of non-adherent cells. Thereafter, medium was changed every 2-3 days; and the cells were cultured for 10-14 days before passage. For passaging, cells were lifted with 0.25% Trypsin/EDTA, counted using Trypan blue and replated at about $0.5$-$1 \times 10^4$ cells/cm$^2$. Subsequent passages (up to 3) were performed when cultures reached 70-80% confluence, which occurred within 4-7 days after re-plating.

Example 2: Correlation Between Expression of Alpha Smooth Muscle Actin (αSMA) and Cell Proliferation in MSC Cultures To elucidate the relationship between αSMA expression and colony growth, and thereby determine whether measurement of α-SMA levels could be used as part of a method to predict proliferative capacity, cell proliferation rate and α-SMA levels were measured in colonies of bone marrow cells ten days after plating.

Cell proliferation assays were conducted on colonies using the Click-iT® Plus EDU Alexa Fluor 594 Imaging kit (Life Technologies, Carlsbad, Calif.) according to the manufacturer's protocol. Cells were labeled with 5-ethynyl-2'-deoxyuridine (EDU) for 5 hrs. After EDU detection, the colonies were blocked with 0.3% Normal Donkey serum and probed with FITC-conjugated anti-αSMA monoclonal antibody (Sigma, St. Louis, Mo.), for one hour, followed by washing. Nuclei were counterstained using Hoechst 33342.

To quantify the percentage of EDU-positive nuclei, images of colonies were acquired using a Cytation 5 plate reader at 1.25× magnification and analyzed using GenS software (BioTek Instruments, Winooski, Vt.). The data for the colonies were then sorted in Excel. Colonies exhibiting highest and lowest EDU incorporation (3-4 colonies/group) were selected and acquired, under 4× magnification, to visualize and quantify αSMA mean fluorescence intensity using ImageJ as mean gray value with the subtraction of the corresponding background. For the analysis of αSMA and EDU distribution in a single colony, an image of the colony was digitally enlarged and αSMA-positive areas were selected; then areas of equal size were selected in αSMA-negative region of the colony. Total nuclei and EDU-positive nuclei were manually counted in these areas.

Figure 1B:
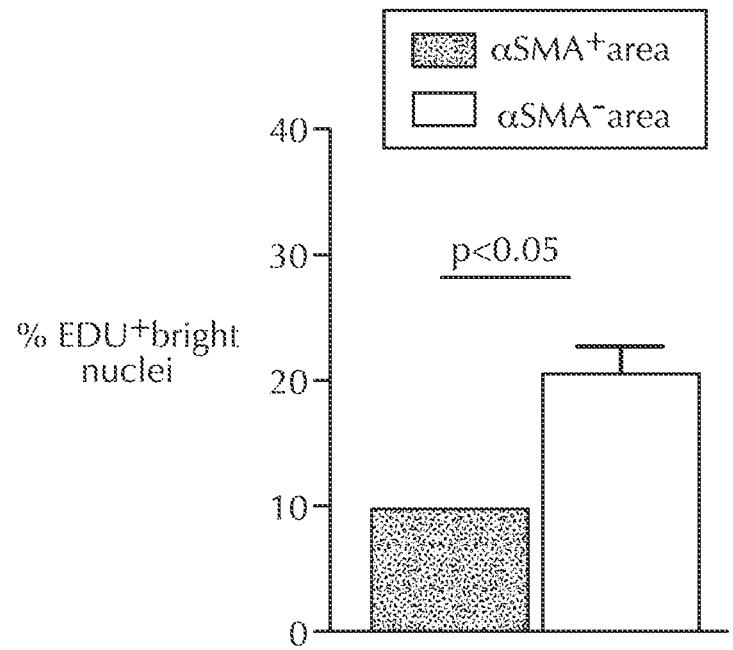
FIG. 1B shows percentage of nuclei staining strongly for EDU in two regions of a colony exhibiting variable levels of α-SMA expression: one region that is high in α-SMA (αSMA⁺ area, stippled bar) and one region that is low in α-SMA (αSMA⁻ area, white bar). Error bars indicate standard deviation between values obtained for the two regions.

Cell lots characterized by a wide range of αSMA expression among colonies were evaluated. Microscopic observations indicated that highly proliferative colonies (i.e., those having a high percentage of EDU-positive nuclei) exhibited lower levels of αSMA expression than did colonies with a lower percentage of EDU-positive nuclei. In 2 lots of cells (AC12 and AC13), colonies with the highest percentage of EDU-positive nuclei (>39% for AC12 and >28% for AC13) and the lowest percentage of EDU-positive nuclei (<18% for AC12 and <15% for AC13) exhibited correspondingly low and high mean fluorescence intensity for αSMA (FIG. 1A). Furthermore, within colonies that had variable levels of αSMA expression, there was a negative correlation between the level of αSMA expression and the percent of nuclei with bright EDU staining (FIG. 1B). αSMA-positive, but not αSMA-negative, areas also contained nuclei with very low levels of EDU in addition to brightly stained ones. Taken together, these observations indicated that the process of EDU incorporation was slower in αSMA-positive cells. Thus, αSMA expression is negatively correlated with both the colony's overall proliferation rate and the proliferation status within the colony.

Example 3: Effects of Fixation and Permeabilization on Detection of LDH Activity To determine whether αSMA expression in MSC colonies is related to the lot growth potential, a robust assay that measures αSMA in a colony and normalizes its expression to the number of cells in the colony was developed using passaged MSCs. A colorimetric assay for intracellular LDH activity was chosen as a surrogate for cell number. Prior observations suggested that cells fixed lightly with formalin retain a substantial proportion of intracellular LDH activity. See also Baba et al. (1971) *J. Cell. Biol.* 51:621-635. Accordingly, the effect of fixation and permeabilization conditions on LDH detection was examined in passaged MSCs, between passages 2 and 4. For these studies, MSCs were counted and plated into 96 well plates at 4, 1.3, and 0.4×10³ cells/well. Next day, the cultures were fixed for either 20 or 40 min, then permeabilized for 20 min and washed. In another set of experiments, cells were fixed for 20 min and permeabilized for 0, 20, or 40 min, and then washed. The residual LDH activity was determined as described below. Cell number was determined using Trypan Blue staining of cultures.

Figure 2A:
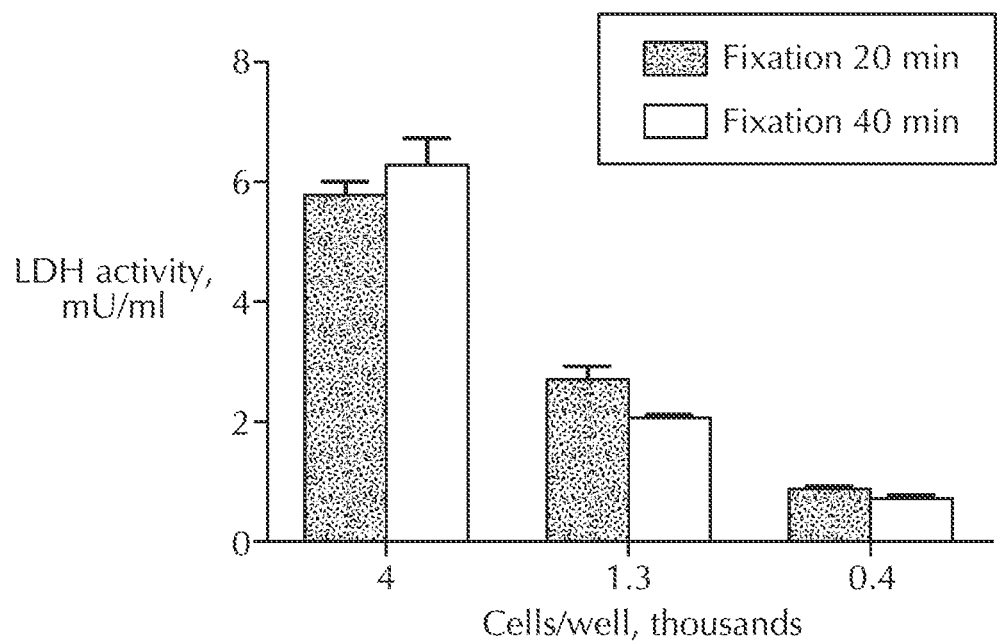
FIG. 2A shows levels of LDH activity in cultured MSCs, plated at three different densities (0.4, 1.3 and $4.0 \times 10^3$ cells/well), that had been fixed with formalin for 20 min (stippled bars) or 40 min (white bars), then permeabilized with Triton X-100 for 20 min.
Figure 2B:
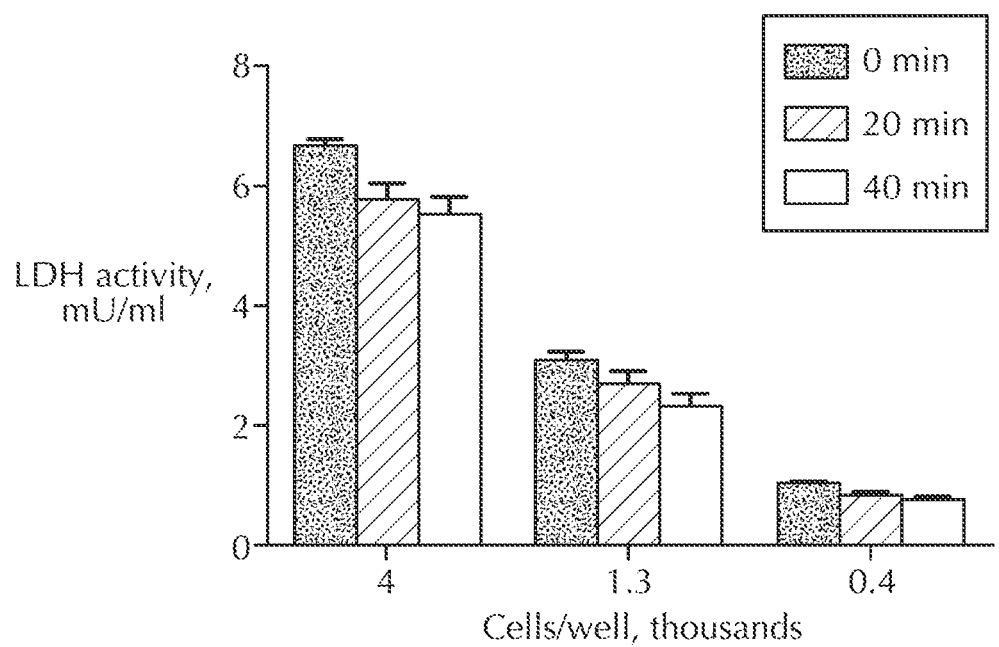
FIG. 2B shows levels of LDH activity in cultured MSCs, plated at three different densities (0.4, 1.3 and $4.0 \times 10^3$ cells/well), that had been fixed with formalin for 20 min then assayed without being permeabilized (stippled bars) or permeabilized with Triton X-100 for 20 min (crosshatched bars) or 40 min (white bars).

The results of these experiments showed that, with a standard 20-minute fixation, LDH activity was proportional to cell number; moreover, increasing fixation time to 40 min had no significant detrimental effect on LDH activity (FIG. 2A). When cells fixed in formalin for 20 minutes were further permeabilized with Triton-X100 for different amounts of time, the LDH activity detected after permeabilization was slightly reduced, depending on the length of the permeabilization period; with an approximately 10-15% reduction for every 20 min of permeabilization between 0 and 40 min (FIG. 2B).

Figure 2C:
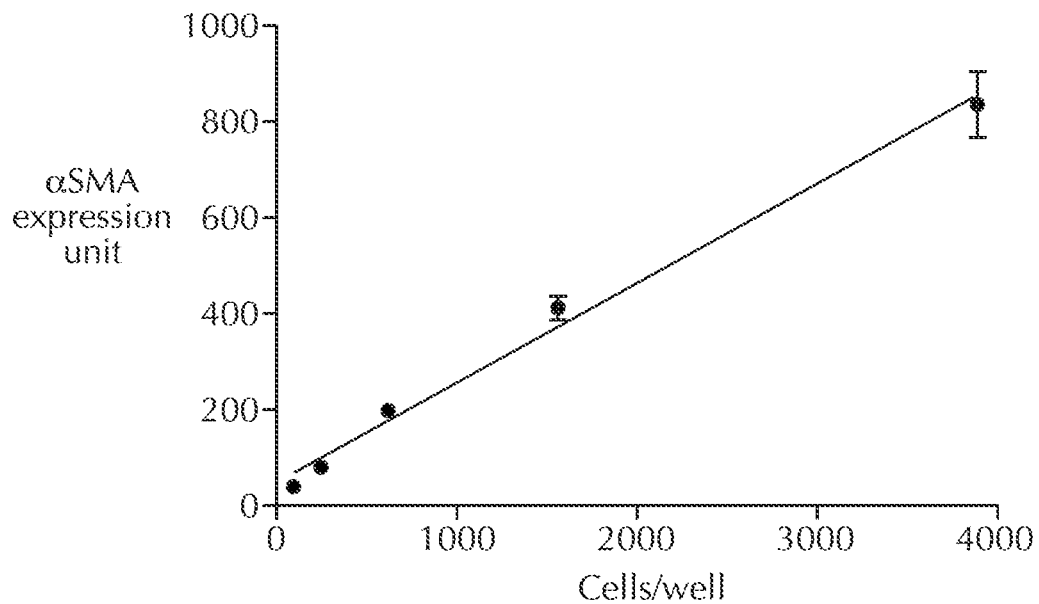
FIG. 2C shows levels of αSMA immunoreactivity (HRP activity) for different concentrations of cultured MSCs following 20 min of fixation and 20 min of permeabilization. The line represents a linear regression fit of the data.
Figure 2D:
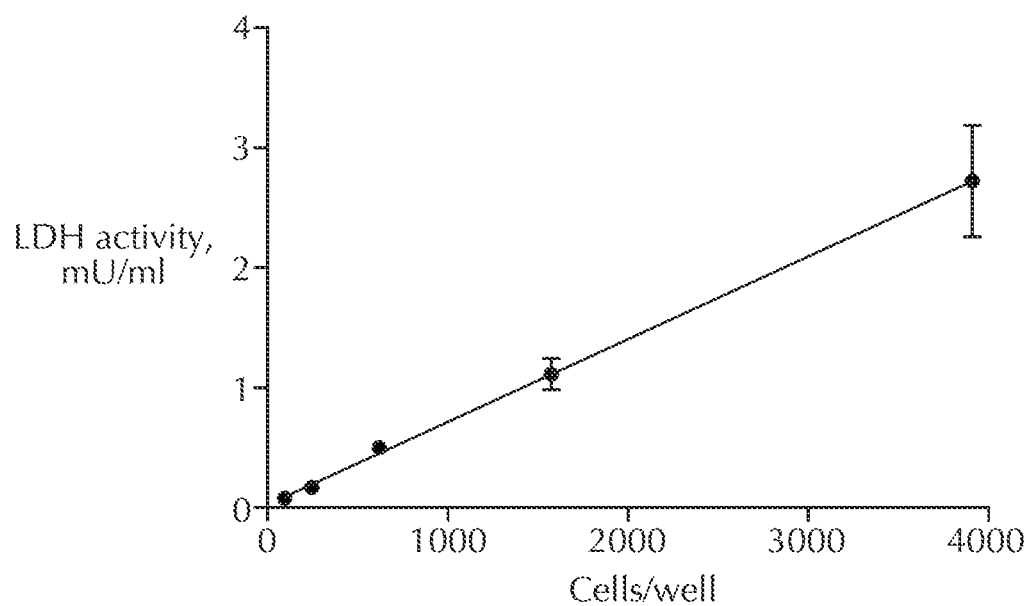
FIG. 2D shows levels of LDH activity for different concentrations of cultured MSCs following 20 min of fixation, 20 min of permeabilization, and one hour of incubation with HRP-conjugated anti-αSMA. The line represents a linear regression fit of the data.
Figure 2E:
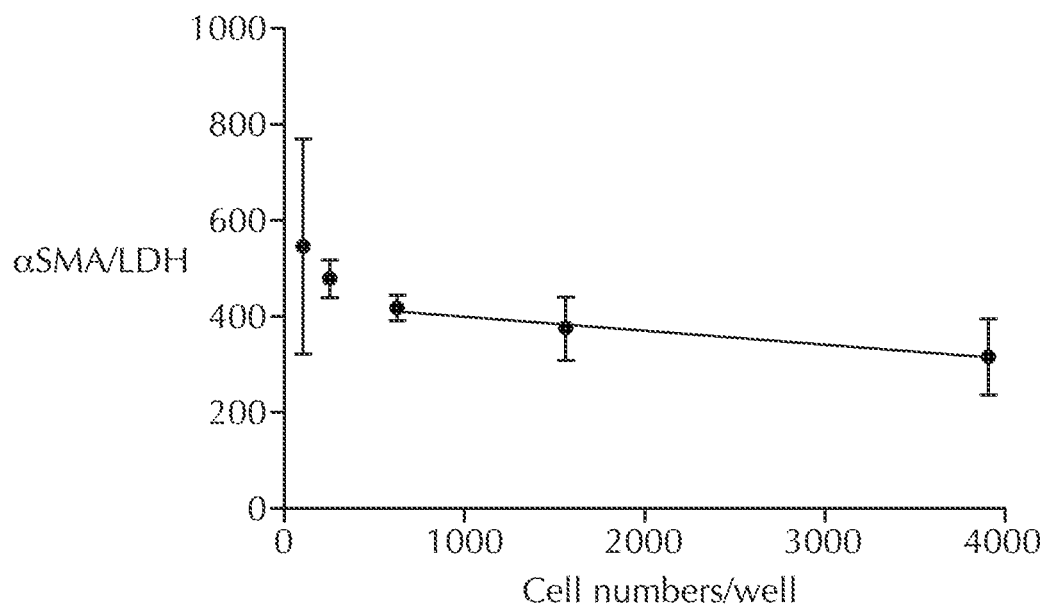
FIG. 2E shows αSMA expression values (obtained from FIG. 2C) normalized to LDH activity values (obtained from FIG. 2D) for various concentrations of cultured MSCs. The line represents a linear regression fit of the data for wells having more than 250 cells per well.

Example 4: Detection of LDH Activity and αSMA Levels in the Same Colony and Correlation with Cell Number Based on the observed retention of LDH activity following fixation (Example 3), it was deemed possible to process cells for intracellular immunocytochemical detection of αSMA, followed by detection of LDH activity in the same cells, using selected fixation and permeabilization times. To confirm this idea, MSCs between passages 2-4 were plated in a 96-well microtiter plate at different cell densities. One day later, cells were fixed for 20 min, permeabilized for 20 min, and reacted with HRP-conjugated anti-αSMA antibody for one hour. After binding of the antibody, intracellular LDH activity was detected, followed by a colorimetric detection of HRP activity. Under these conditions, LDH and αSMA values were proportional to plated cell numbers (FIGS. 2C and 2D). αSMA expression values were then normalized to corresponding LDH activity values to obtain an "αSMA/cell" value. For cell concentrations >250 cells/well, the normalization provided a constant value, as expected; below concentrations of 250 cells/well, the normalization produced variable results (FIG. 2E).

After the initial assay development using passaged MSCs, described above, the assay was further characterized in CFUf colonies. On day 10 after plating of bone marrow cells, LDH activity in colonies was measured, and the number of nuclei per colony were quantified by image analysis of colonies stained with Hoechst 33342 (Molecular Probes, Eugene, Oreg.) using a Cytation 5 multi-mode plate reader (BioTek, Winooski, Vt.) at four-fold magnification and GenS software (BioTek).

Figure 2F:
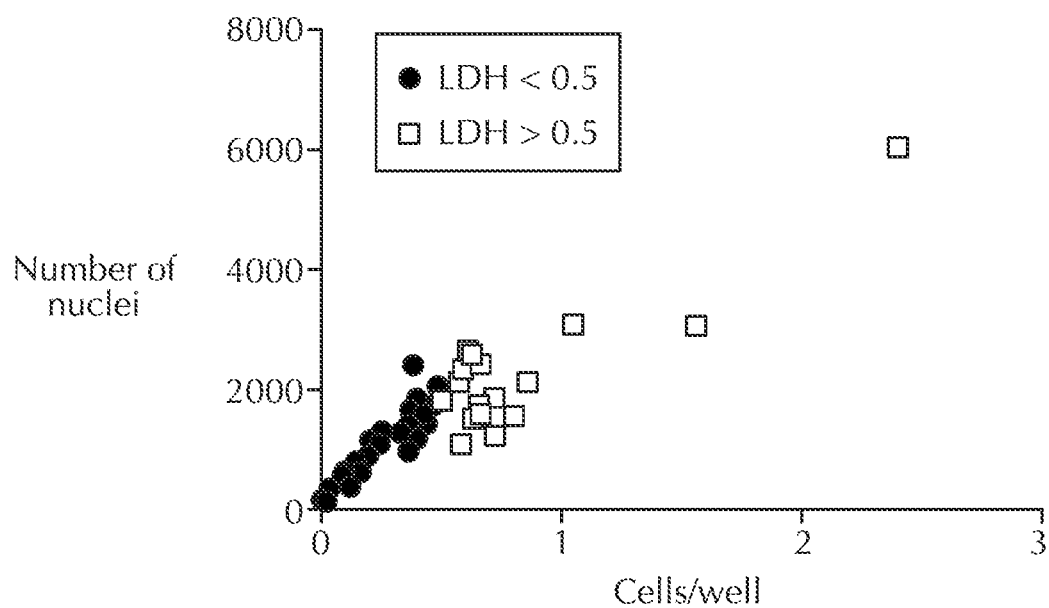
FIG. 2F shows the relationship between cell density (represented by LDH activity) and observed number of nuclei (as detected by Hoechst staining) in 10-day CFU-f colonies. Values for colonies having LDH activities of <0.5 mUnits/ml (black circles) and >0.5 mUnits/ml (white squares) are highlighted.

For colonies containing up to 2500 nuclei, a linear relationship between LDH values and the number of nuclei was observed. However, for colonies containing 2500 nuclei (corresponding to ~0.5 mU/ml LDH) or more, some colonies appeared to have fewer nuclei than expected based on a linear regression (FIG. 2F). Microscopic examination showed that colonies having >2500 cells had a high chance of being partly located in the blind area of the microscope field (about 20% of the microtiter well). Thus the observed number of nuclei likely underestimates the number of cells in large colonies, while LDH activity seemed to be a more accurate indicator of cell number. Based on the data presented in FIG. 2F, a LDH activity of 0.4 mU/ml corresponded to a colony of ~1,000 cells. This value was chosen as an arbitrary threshold for large colonies.

Example 5: Assaying Multiple Colonies for αSMA and LDH (ALC Assay) Methods

Based on the results described above, two colorimetric assay protocols—residual LDH activity and αSMA protein expression detection—were incorporated into a single protocol used to assay multiple colonies growing on the same microtiter plate. For these experiments, washed bone marrow cells (obtained as described in Example 1) were resuspended at a concentration of $6.6 \times 10^4$ WBCs/ml and plated (100 μl of cell suspension per well) into 96-well black microplates with clear bottoms (Costar®). Wells designated for α-SMA and LDH standards, and for Horseradish Peroxidase (HRP) controls, were kept unused until indicated in the protocol below. Plating at this density resulted in growth of colonies in less than 30% of wells; thus ensuring a low probability of having more than 1 colony per well.

Nine days after plating, microtiter plates were microscopically examined using phase contrast and wells with colonies were marked. On day 10, plates were washed with PBS, fixed with 4% paraformaldehyde (PFA) for 20 min; then the fixative was replaced with PBS. Meanwhile, surrogate αSMA standards were prepared by serially diluting AffiniPure Donkey Anti-Mouse IgG (Jackson Immunoresearch, West Grove, Pa.) in PBS and adsorbing the solutions in the designated wells for 1 hr; these wells were then blocked with MSC growth medium. All wells (except for those designated for LDH and αSMA standards and HRP controls) were then washed once with PBS and incubated with 0.2% Triton X-100 in PBS for 20 min, followed by blocking in 0.5% Normal Donkey Serum (Jackson Immunoresearch, West Grove, Pa.) for 30 min. The wells (except for those designated for LDH standards and HRP controls) were then incubated with a HRP-conjugated monoclonal anti-αSMA antibody (1/1000 dilution; Abcam, Cambridge, Mass.) for 1 hr and washed 3 times with PBS.

The LDH assay was then performed. First, LDH standards were prepared in designated wells by serially diluting bovine LDH (Sigma). Then Catalyst/Dye (0.25 ml/11 ml) mixture from the LDH Cytotoxicity Detection kit (Clontech Laboratories, Mountain View, Calif.) was added to all wells in which cells had been plated and to the wells containing the LDH standards. Plates were incubated at room temperature for 7-10 min. The signals were read at 490 nm with correction at 650 nm and photometric values were converted to milliUnits LDH activity per ml using SoftMAXPro software.

After LDH detection, plates were washed once with PBS and prepared for HRP detection. To ensure that readings on all plates would be comparable among different experiments, an HRP control prepared from highly stabilized HRP (Sigma) was used on each plate. Wells in which cells had been plated, wells containing surrogate αSMA standards, and HRP controls were filled with the HRP substrate 3,3',5,5'-Tetramethylbenzidine (TMB, eBioscience). Absorbance was measured at 370 nm with correction at 492 nm, and photometric values were converted to ng/ml of bound antibody. Both LDH and HRP signals were quantified using standard curves generated in SoftMax Pro (Molecular Devices, Sunnyvale, Calif.). LDH activity was expressed in mU/ml. αSMA expression was expressed as the corresponding concentration of anti-αSMA antibody in ng/ml.

Data Processing

The processing of ALC assay data was conducted using a programmed Excel template. HRP control data were used to make adjustments between different plates and experiments if needed. Then, for each plate, background values for both measured parameters were calculated: for LDH, as the average of all wells without a colony+1 standard deviation (SD), and for HRP, as the average of all wells without colonies. Then the background was subtracted from the corresponding dataset. This method enabled the elimination of wells with less than 50 cells from further calculations; at the same time, less stringent conditions for HRP signals prevented the exclusion of colonies with very low levels of αSMA expression. Then αSMA expression was normalized to the corresponding LDH signal from the same well (a surrogate for αSMA/cell). All colony data were sorted from high to low LDH levels and the percentage of colonies with LDH>0.4 mU/ml ("Large Colonies") was determined. This threshold typically categorized more than 15% of the colonies as Large Colonies in the BM lots. In these Large Colonies, normalized αSMA expression was averaged. Each BM lot was thus characterized by the average αSMA level in cells of Large Colonies (termed here as Av(αSMA/LDH)$_{LC}$) and the percentage of large colonies.

Statistics

Statistical analysis (paired or unpaired t-test and linear regression analysis) and graphing were done using Prism 6 software (GraphPad, San Diego, Calif.). $p<0.05$ was considered statistically significant.

Results

Figure 3A:
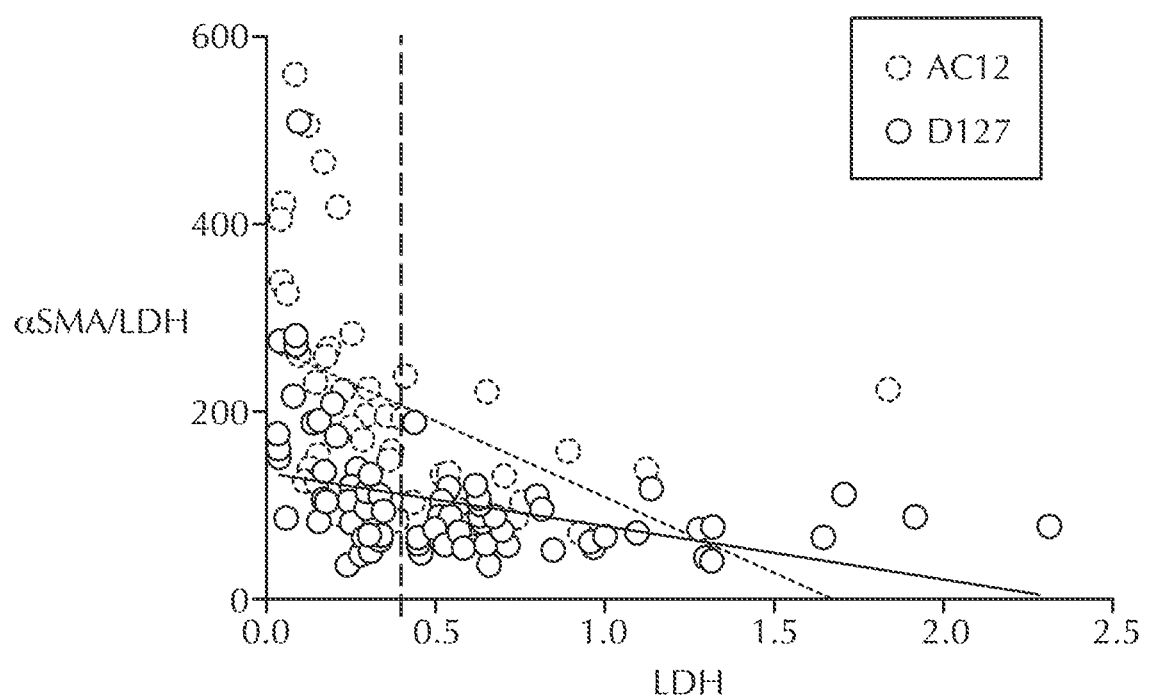
FIG. 3A shows normalized αSMA values (αSMA/LDH) plotted against colony size (represented by LDH activity) for individual colonies generated by cells obtained from two different donors: AC12 (dotted circles) and D127 (closed circles). Each circle represents an individual colony. The dotted line represents the linear regression fit for colonies generated by cells obtained from donor AC12. The solid line represents the linear regression fit for colonies generated by cells obtained from donor D127. The dashed vertical line represents the arbitrarily-selected threshold value for Large Colonies of 0.4 mU/ml LDH activity.

Ten BM MSC lots, producing 34-89 colonies (median 52) per lot, were analyzed ten days after plating (Day 10). For 9 out of the 10 lots, plotting the LDH value (surrogate for cell number) for each colony against its corresponding normalized αSMA/LDH value (surrogate for average amount of αSMA per cell) yielded a negative correlation between the size of each colony and its αSMA/cell ($p<0.05$). Furthermore, the distribution of LDH vs. αSMA/LDH values was characteristic for each lot of cells, and thus this distribution can be used to discriminate among different lots. Exemplary data from two lots of cells (obtained from donors AC12 and D127) is shown in FIG. 3A.

Due to the exponential nature of cell growth, the contribution of large colonies to cell number in mass cultures is substantially greater; and that of small colonies is essentially negligible; even if all colonies are growing at the same rate. Therefore, the present invention defines Large Colonies as those with LDH values≥0.4 mU/ml at Day 10 (i.e., colonies containing approximately 1,000 cells, meaning their CFUf progenitor had undergone about 10 cell doublings in 10 days).

Figure 3B:
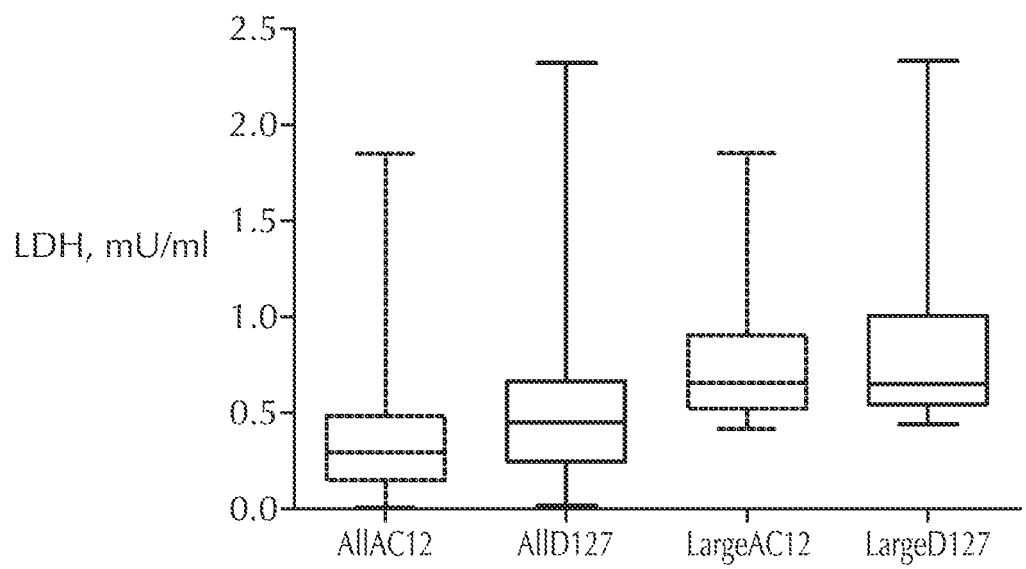
FIG. 3B is a box and whiskers plot of LDH values for MSC colonies obtained from two donors (AC12 and D127). Values for all colonies (All) and for colonies having >0.4 mU/ml LDH (Large) for both lots are provided.
Figure 3C:
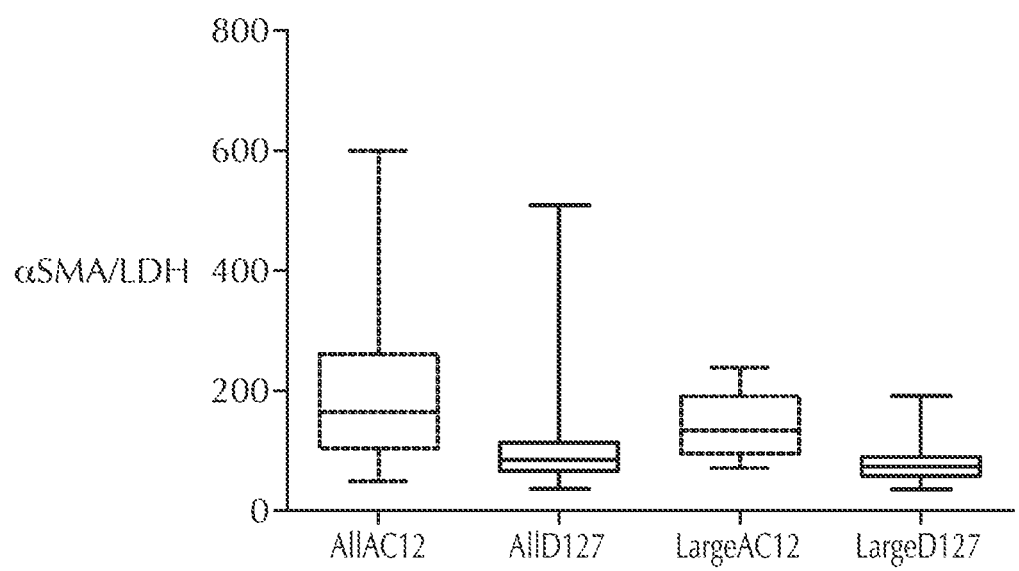
FIG. 3C is a box and whiskers plot of αSMA/LDH values for MSC colonies obtained from two donors (AC12 and D127). Values for all colonies (All) and for colonies having >0.4 mU/ml LDH (Large) for both lots are provided.

Analysis of LDH and αSMA/LDH values for two lots of cells (AC12 and D127) are presented in FIGS. 3B and 3C. The values were obtained for all colonies; and for only Large Colonies as defined above. As expected, large colonies contain, on average, higher LDH levels than the cell population as a whole (FIG. 3B). In addition, the αSMA/LDH values for large colonies are more narrowly distributed than those for the culture as a whole, and allow cultures from the two donors to be distinguished (FIG. 3C).

Figure 4:
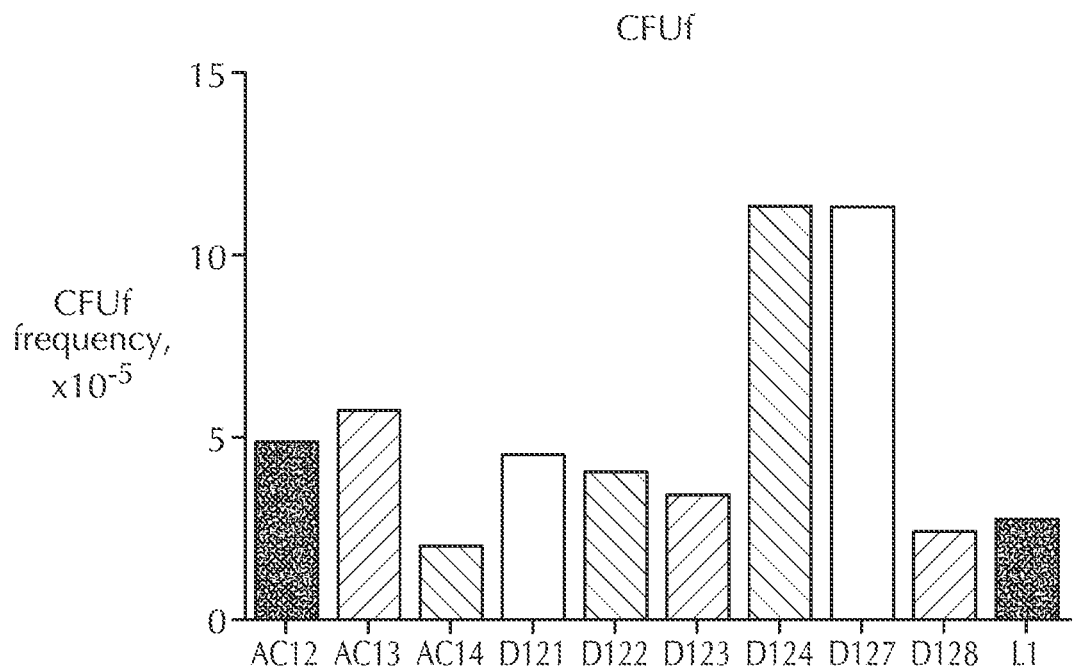
FIG. 4 shows colony forming efficiencies (CFUf frequencies) for ten lots of cultured bone marrow cells. CFE (colony-forming efficiency) is expressed as number of colonies per $10^5$ white blood cell equivalents that were plated at a concentration of $6.6 \times 10^4$ cells/ml.
Figure 5:
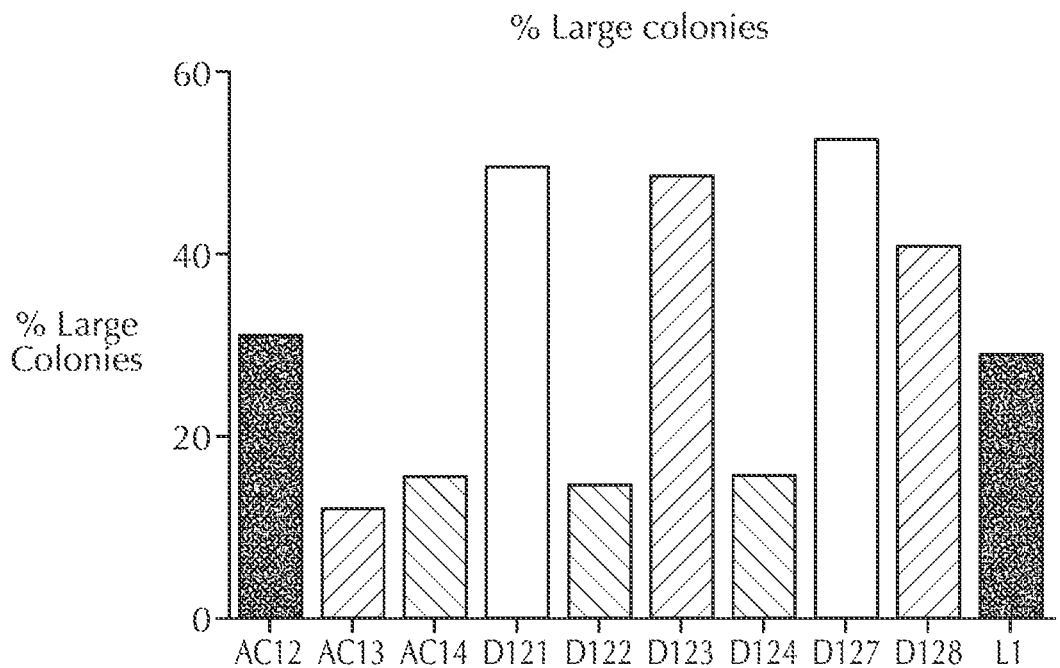
FIG. 5 shows percentage of large colonies (i.e., colonies having LDH levels ≥0.4 mU/ml) for ten lots of cultured bone marrow cells.
Figure 6:
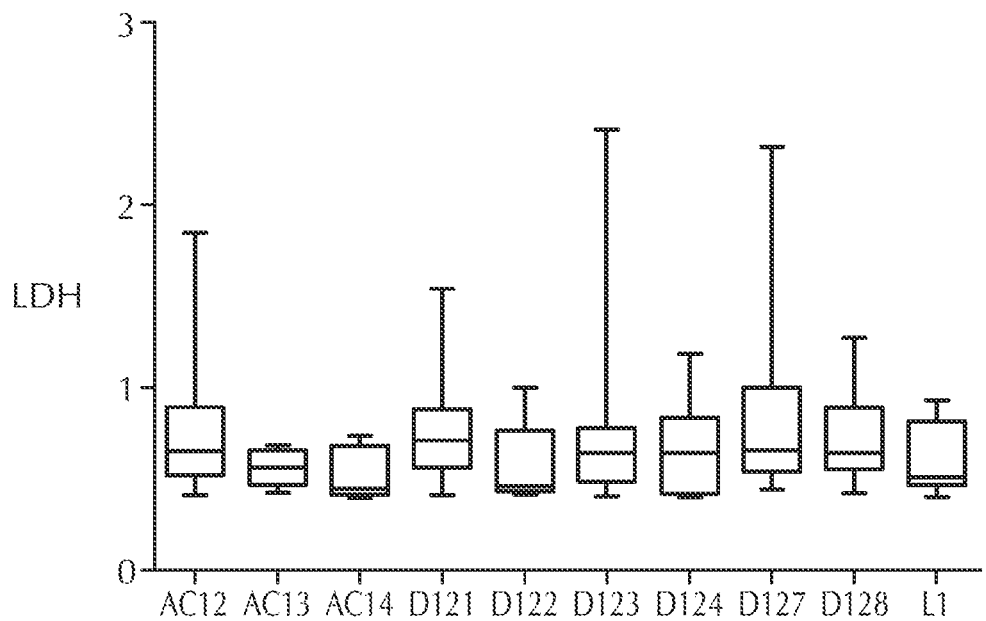
FIG. 6 shows LDH levels (a surrogate marker for cell size), in box and whiskers format, for ten lots of cultured bone marrow cells.
Figure 7:
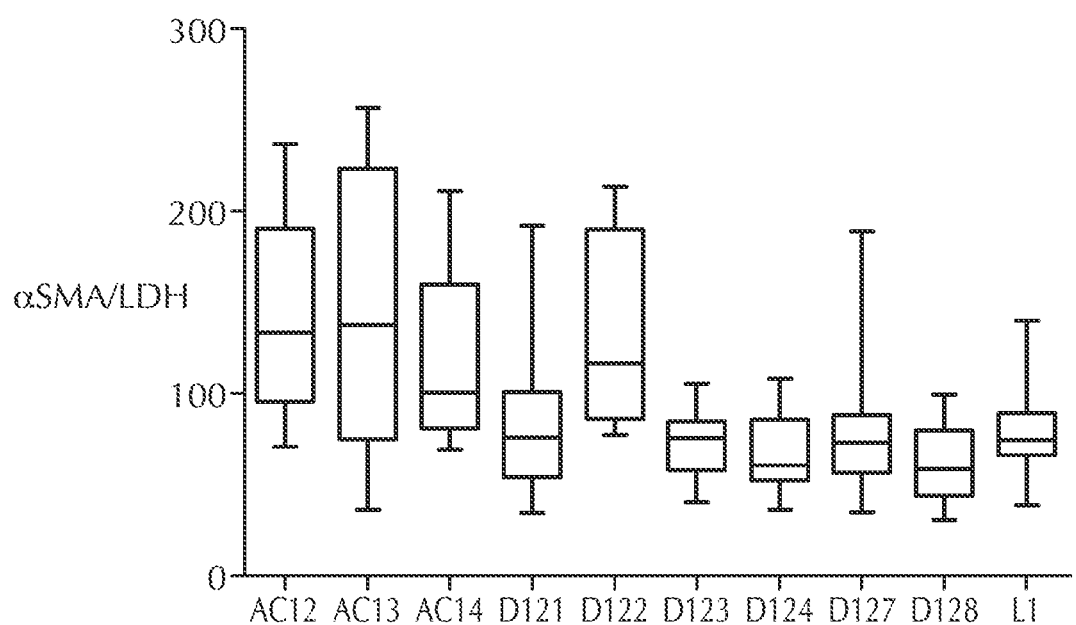
FIG. 7 shows αSMA/LDH values, in box and whiskers format, for ten lots of cultured bone marrow cells.

Example 6: Correlation of Day 10 ALC Assay Results with Growth Potential of Mass Cell Cultures Ten lots of MSCs were grown in mass culture for three passages. For each of these lots, CFUf plating efficiency (FIG. 4), percent of Large Colonies (defined as those with LDH>0.4 mU/ml, FIG. 5), the distribution of Large Colonies by size (LDH, FIG. 6) and normalized αSMA in each colony (αSMA/LDH, FIG. 7) were determined.

Figure 8A:
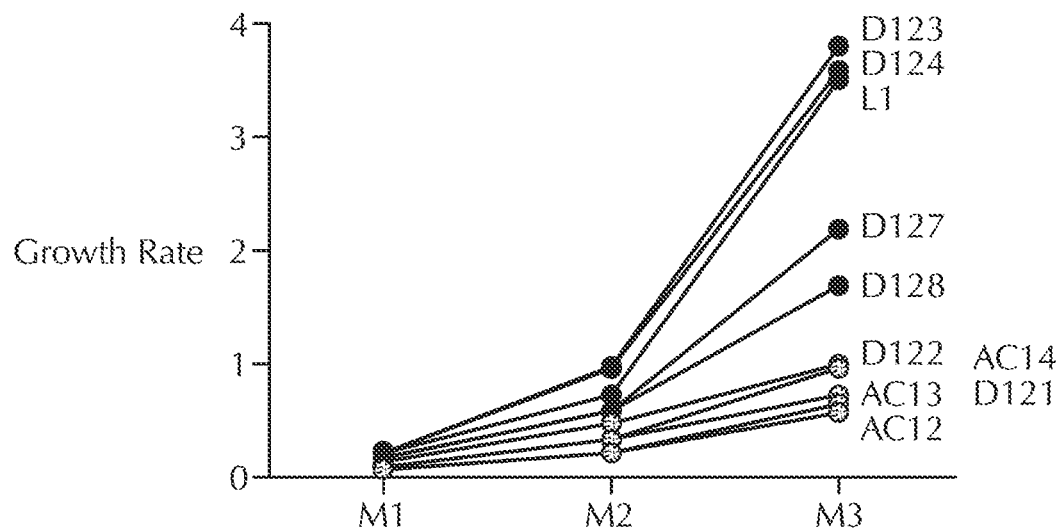
FIG. 8A shows the growth rate (calculated as described in Example 6) for ten lots of cultured MSCs, assessed at three passages (passage M1, passage M2 and passage M3)

The growth rate (GR) of the cells in each of the ten lots was also determined, using the following calculation:

$$GRn = dH_0/dWBC \times dH_1/dP_1 \times \ldots \times dH_n/dP_n$$

where $dH_n$ is the cell density at harvest of passage n; $dP_n$ is the cell density at plating of passage n; and dWBC is the cell density at initial BM plating. Analysis of growth rates revealed that a MSC lot could be categorized, based on its cumulative growth rate (GR) at passage 3, as either slow-growing (GR<1) or fast-growing (GR>1). See FIG. 8A.

Figure 8B:
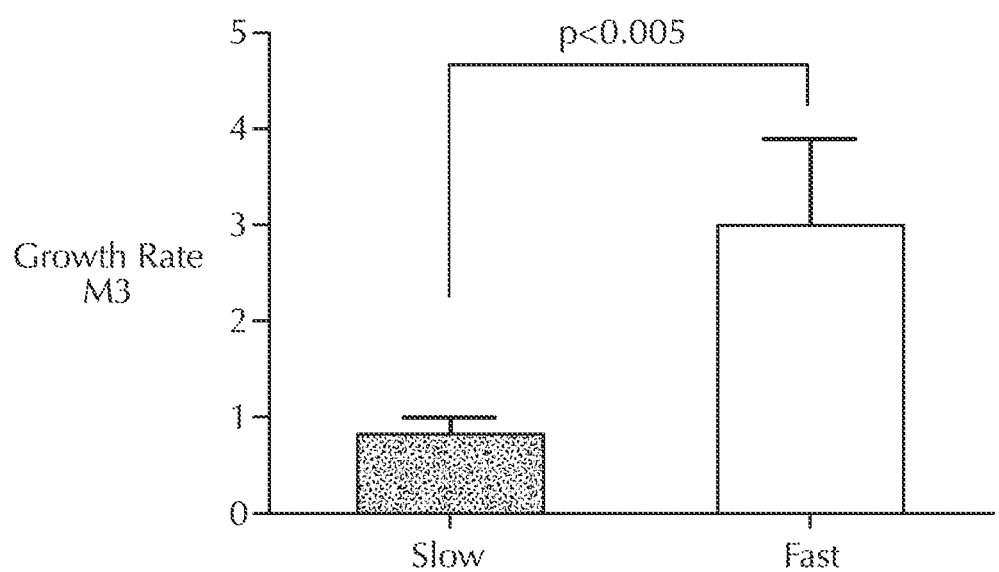
FIG. 8B shows a comparison of growth rates, at third passage (M3), for slow-growing cultures (GR≤1, left bar) and fast-growing cultures (GR>1, right bar).
Figure 8C:
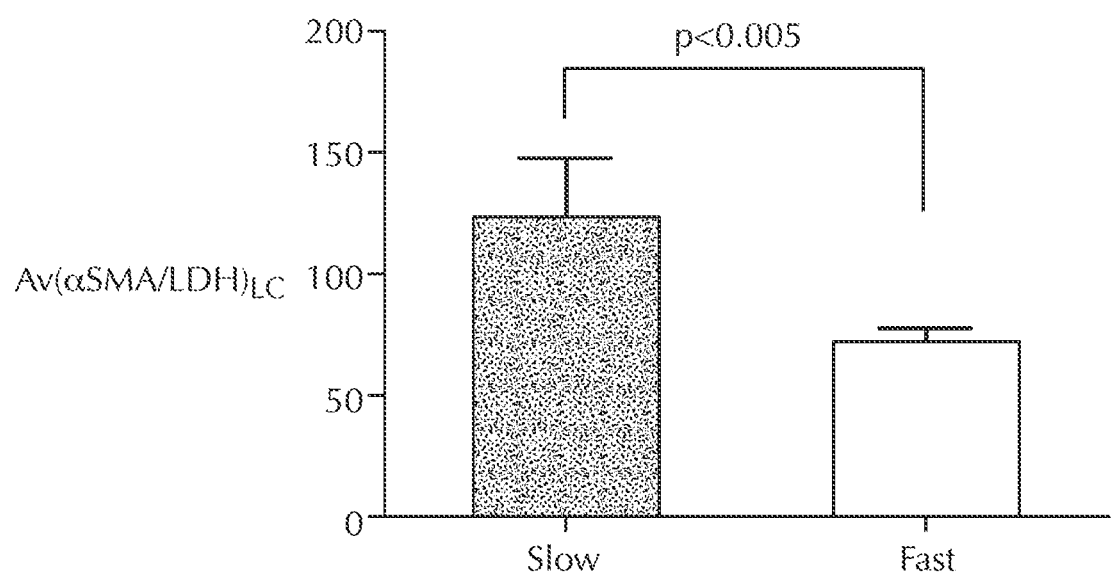
FIG. 8C shows normalized αSMA values (i.e., $Av(αSMA/LDH)_{LC}$) for slow-growing cultures (GR≤1, left bar) and fast-growing cultures (GR>1, right bar) at ten days after plating.

Analysis of growth rate at the third passage, using a growth rate of >1 as the threshold value for a fast-growing culture, revealed that the difference in growth rate between slow-growing and fast-growing cultures was statistically significant (FIG. 8B). MSC growth data were compared to CFE, percent of large (LDH>0.4 mU/ml) colonies, and Av(αSMA/LDH)$_{LC}$. No correlation was detected between either CFE, or percentage of Large Colonies, and mass culture growth. However, slow-growing lots (GR<1) had significantly higher Av(αSMA/LDH)$_{LC}$ than did fast growing lots (FIG. 8C). When large colonies are defined as those with LDH>0.4, the statistical difference in Av(αSMA/LDH)$_{LC}$ values between slow-growing lots and fast-growing lots was p<0.005 and $R^2$=0.71.

When growth rate of mass cultures was plotted against their Av(αSMA/LDH)$_{LC}$ values, a significant linear correlation was observed (slope non-zero with p<0.02, $R^2$=0.514). When percentage Large Colonies was plotted against Av(αSMA/LDH)$_{LC}$, all data points fell into two groups: one consisted of 4 lots of cells that all exhibited slow growth, and the other contained all 5 fast growing lots (plus a slow growing lot, that was likely unintentionally overgrown at passage 2). These initial data suggested that an Av(αSMA/LDH)$_{LC}$ value >100 predicted subsequent slow growth of a mass culture with 100% positive and 80% negative predictive value; and with 100% specificity and 83% sensitivity.

Figure 9A:
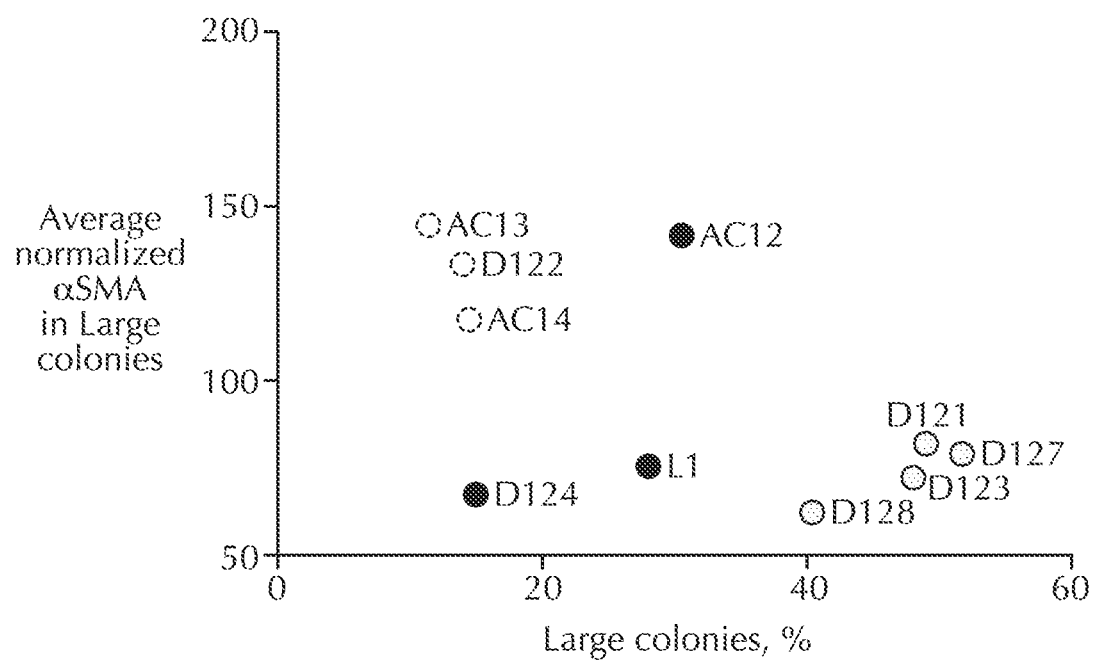
FIG. 9A shows normalized αSMA values (i.e., αSMA/LDH) in large colonies as a function of percentage of large colonies for ten different lots of cultured bone marrow cells.

Based on the results described above, to provide the most effective correlation between ALC data and growth potential for a given lot of MSCs, the ALC data obtained for colonies from each lot were reduced to two representative and functional parameters: (1) percentage of large colonies and (2) average αSMA/LDH values of these large colonies. Using this method for data reduction, colony data from 10 lots was plotted and compared on a "Predictor Plot" showing Av(αSMA/LDH)$_{LC}$ (i.e., average normalized αSMA) values in Large Colonies as a function of the percentage of Large Colonies in the culture (FIG. 9A). Cell lots having a higher growth potential are expected to have a high percentage of large colonies, and low αSMA/LDH values; thus, when Av(αSMA/LDH)$_{LC}$ is plotted against percentage of large colonies, the values are expected to cluster in the lower right region of the Predictor Plot. Conversely, lots prone to early growth slowdown are expected to have values located at the upper left area of the plot.

Figure 9B:
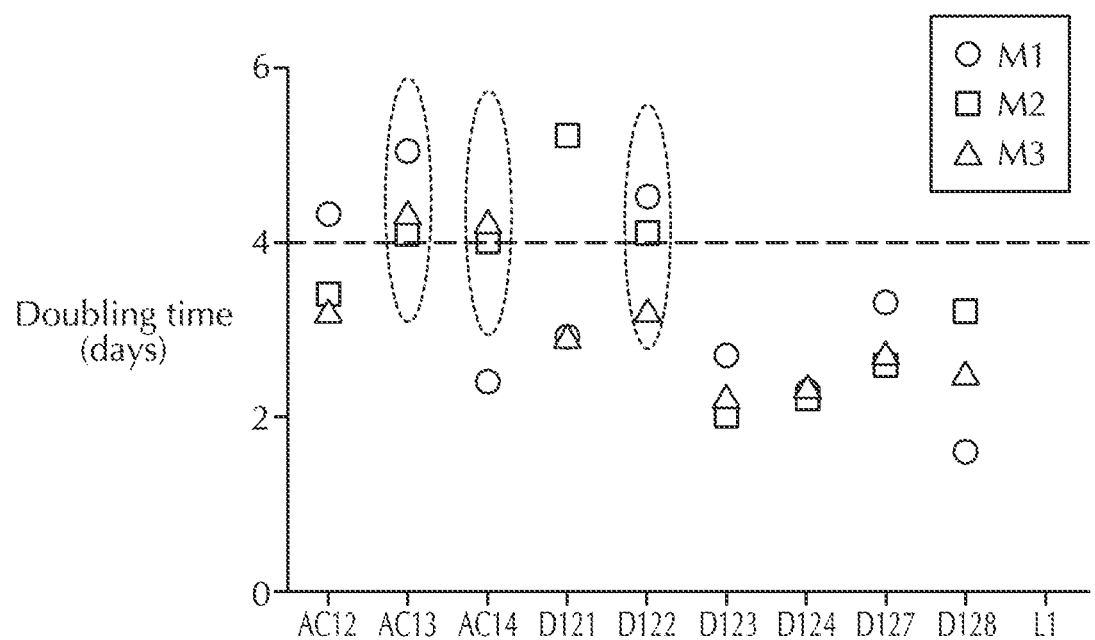
FIG. 9B shows the doubling time for the same ten cell cultures shown in FIG. 9A, assessed at three passages (M1, M2 and M3).

To test the predictive value of the Av(αSMA/LDH)$_{LC}$ vs. percentage large colonies plot, ten lots of MSCs were grown in mass culture, up to passage 3, and αSMA, LDH and percentage large colonies (i.e., colonies with LDH values≥0.4 mU/ml) were obtained for each lot. Av(αSMA/LDH)$_{LC}$ values were then plotted against LDH values for each of the lots (FIG. 9A). Doubling times were calculated for each of the ten mass cultures; these are shown in FIG. 9B.

When the Av(αSMA/LDH)$_{LC}$ vs. percentage large colonies value for each lot was compared with its growth rate, the results indicated that the Av(αSMA/LDH)$_{LC}$ vs. percentage large colonies value predicts the growth potential of a MSC cell lot. For example, the three lots of MSCs whose Av(αSMA/LDH)$_{LC}$ vs. percentage large colonies values clustered nearest the upper left region of the plot in FIG. 9A (lots AC13, AC14 and D122) were among those with the longest doubling times (>4 days, FIG. 9B). Conversely, lots D121, D123, D127 and D128, whose Av(αSMA/LDH)$_{LC}$ vs. percentage large colonies values clustered in the lower right region of the plot in FIG. 9A, were among those with the shortest doubling times (FIG. 9B).

What is claimed is:

1. A method for selecting a lot of mesenchymal stromal cells (MSCs) with a high proliferative capacity, from among a plurality of lots of bone marrow suspension; the method comprising:
   (a) separately plating a sample of cells from each lot of bone marrow suspension at low density to form a culture comprising single colonies;
   (b) measuring α-smooth muscle actin (α SMH) levels in each colony, expressed as ng/ml anti-αSMA antibody bound to a colony;
   (c) measuring lactate dehydrogenase (LDH) levels in each colony, expressed as milliUnits/ml (mU/ml) LDH activity;
   (d) determining the percentage of large colonies in the culture, wherein a large colony is a colony in which the sum of the intracellular LDH values of all cells in the colony is greater than 0.4 mU/ml;
   (e) determining the αSMA/LDH ratio (normalized αSMA value) in each large colony;
   (f) determining an average of the normalized αSMA values for all large colonies in the culture (Av(αSMA/LDH)$_{LC}$) which is expressed as a function of the percentage of large colonies in the culture;
   (g) selecting a culture with an Av(αSMA/LDH)$_{LC}$ value of 100 or less and a percentage of large colonies that is 40% or greater which represents a lot of MSCs with a high proliferative capacity; and
   (h) further comprising growing MSCs selected with the high proliferative capacity as determined in step (g) in mass culture.

2. The method of claim 1, wherein the measurements of steps (b) and (c) are conducted ten days after plating the cells in step (a).

3. The method of claim 1, wherein said lot or lots with high proliferative capacity are used in a process for manufacturing a therapeutic derivative of MSCs.

4. The method of claim 1, further comprising transfecting the MSCs in mass culture with a polynucleotide comprising sequences encoding a Notch intracellular domain, wherein the polynucleotide does not encode full-length Notch protein.

5. A method for selecting a lot of mesenchymal stromal cells (MSCs) having a high proliferative capacity, the method comprising:
   (a) plating a sample of MSCs at low density;
   (b) culturing the MSCs so that single colonies are formed;
   (c) measuring αSMA levels in each colony, expressed as ng/ml anti-αSMA antibody bound to a colony;
   (d) measuring LDH activity in each colony;
   (e) determining the number of large colonies in the culture, wherein a large colony is a colony in which the sum of the intracellular LDH values of all cells in the colony is greater than 0.4 milliUnits/ml;
   (f) normalizing the level of αSMA to the level of LDH activity in the large colonies, to obtain an average αSMA/LDH value for the large colonies;
   (g) expressing the average αSMA/LDH value for the large colonies as a function of the percentage of large colonies in the culture; and
   (h) selecting a culture having:
      (i) an average αSMA/LDH value for large colonies of 100 or less, and
      (ii) a percentage of large colonies that is 40% or greater; and further comprising growing MSCs selected with the high proliferative capacity as determined in step (h) in mass culture.

6. The method of claim 5, wherein the measurements of steps (c) and (d) are conducted ten days after plating the cells in step (a).

7. The method of claim 5, wherein said lot or lots with high proliferative capacity are used in a process for manufacturing a therapeutic derivative of MSCs.

8. The method of claim 5, further comprising transfecting the MSCs in mass culture with a polynucleotide comprising sequences encoding a Notch intracellular domain, wherein the polynucleotide does not encode full-length Notch protein.

* * * * *